(12) United States Patent
Probert et al.

(10) Patent No.: US 11,635,414 B2
(45) Date of Patent: Apr. 25, 2023

(54) METHOD AND APPARATUS FOR CREATING A CLASSIFIER INDICATIVE OF A PRESENCE OF A MEDICAL CONDITION

(71) Applicant: The University of Liverpool, Liverpool (GB)

(72) Inventors: Christopher Simon John Probert, Liverpool (GB); Raphael Bastos Mareschi Aggio, Liverpool (GB)

(73) Assignee: The University of Liverpool, Liverpool (GB)

( * ) Notice: Subject to any disclaimer, the term of this patent is extended or adjusted under 35 U.S.C. 154(b) by 393 days.

(21) Appl. No.: 15/550,734

(22) PCT Filed: Feb. 12, 2016

(86) PCT No.: PCT/GB2016/050344
§ 371 (c)(1),
(2) Date: Aug. 11, 2017

(87) PCT Pub. No.: WO2016/128764
PCT Pub. Date: Aug. 18, 2016

(65) Prior Publication Data
US 2018/0038839 A1    Feb. 8, 2018

(30) Foreign Application Priority Data
Feb. 13, 2015    (GB) .................................... 1502447

(51) Int. Cl.
*G01N 30/86*    (2006.01)
*G16H 50/70*    (2018.01)
(Continued)

(52) U.S. Cl.
CPC ..... *G01N 30/8675* (2013.01); *G01N 30/8686* (2013.01); *G16C 20/20* (2019.02);
(Continued)

(58) Field of Classification Search
CPC ........ G16H 50/20; G16H 50/70; G16C 20/20; G16C 20/70; G01N 30/8675; G01N 30/8686
See application file for complete search history.

(56) References Cited

U.S. PATENT DOCUMENTS 5,885,841 A * 3/1999 Higgs, Jr. ................ C07K 1/12
436/86
7,736,905 B2 * 6/2010 Roder .................. G06K 9/6231
436/173
(Continued)

FOREIGN PATENT DOCUMENTS

| CN | 101929989 A | 12/2010 |
|----|-------------|---------|
| CN | 102006824 A | 4/2011 |

(Continued)

OTHER PUBLICATIONS

Daszykowski et al., "Automated alignment of one-dimensional chromotographic fingerprints", 2010, pp. 6127-6133 (Year: 2010).*
(Continued)

*Primary Examiner* — Shahid Merchant
*Assistant Examiner* — Steven G. S. Sanghera
(74) *Attorney, Agent, or Firm* — Edell, Shapiro & Finnan, LLC

(57) ABSTRACT

An embodiment of the present invention provides a method of creating a classifier indicative of a presence of a medical condition in a subject, comprising receiving chromatogram data indicative of a profile of volatile organic compounds in a sample from each of a first plurality of subjects having the medical condition and a second plurality of subjects without the medical condition, selecting one of the chromatogram data as reference chromatogram data, aligning the remaining chromatogram data in relation to the reference chromatogram data, extracting one or more features from the chromatogram data using a Mexican hat wavelet transform of
(Continued)

one or more scales, selecting one or more features of the chromatogram data indicative of the medical condition, and constructing a classifier for determining a boundary between chromatogram data indicative of the medical condition and chromatogram data indicative of an absence of the medical condition.

27 Claims, 9 Drawing Sheets

(51) Int. Cl.
G16H 50/20 (2018.01)
G16C 20/20 (2019.01)
G16C 20/70 (2019.01)

(52) U.S. Cl.
CPC .............. *G16H 50/20* (2018.01); *G16H 50/70* (2018.01); *G16C 20/70* (2019.02)

(56) References Cited

U.S. PATENT DOCUMENTS

| | | | |
|---|---|---|---|
| 7,873,196 | B2 | 1/2011 | Henschke et al. |
| 8,568,315 | B2 | 10/2013 | Currie et al. |
| 8,580,231 | B2 | 11/2013 | Sukerkar et al. |
| 8,653,242 | B2 | 2/2014 | Neville et al. |
| 8,775,092 | B2 | 7/2014 | Colwell et al. |
| 8,969,310 | B2 | 3/2015 | Beliveau et al. |
| 9,023,811 | B2 | 5/2015 | Mithen et al. |
| 9,102,722 | B2 | 8/2015 | Mueller et al. |
| 9,127,277 | B2 | 9/2015 | Vaishnaw et al. |
| 9,163,282 | B2 | 10/2015 | Rabinowitz et al. |
| 2005/0265629 | A1* | 12/2005 | Fu ..................... G06K 9/00516 382/265 |
| 2007/0055151 | A1* | 3/2007 | Shertukde ................ A61B 7/04 600/437 |
| 2007/0223807 | A1 | 9/2007 | Yankelevitz et al. |
| 2011/0034811 | A1 | 2/2011 | Naujokat et al. |
| 2012/0309048 | A1* | 12/2012 | Ratcliffe ................ G01N 30/74 435/34 |
| 2012/0326092 | A1 | 12/2012 | Haick et al. |
| 2013/0303502 | A1 | 11/2013 | Cavanagh et al. |
| 2014/0193359 | A1 | 7/2014 | Zeng et al. |
| 2015/0051141 | A9 | 2/2015 | Shandler et al. |
| 2018/0003683 | A1* | 1/2018 | Kozawa ............. G01N 30/8631 |

FOREIGN PATENT DOCUMENTS

| | | |
|---|---|---|
| EP | 0898460 | 3/1999 |
| EP | 2265173 A1 | 12/2010 |
| KR | 20130134901 A | 12/2013 |
| WO | 9726823 A1 | 7/1997 |
| WO | 2004008953 A1 | 1/2004 |
| WO | 2007109704 A1 | 9/2007 |
| WO | 2009128000 A1 | 10/2009 |
| WO | 2011061308 A2 | 5/2011 |
| WO | 2011083473 A1 | 7/2011 |
| WO | 2012175916 A1 | 12/2012 |

OTHER PUBLICATIONS

Van Berkel et al., "Development of accurate classification method based on the analysis of volatile organic compounds from human exhaled air", 2007, pp. 101-107 (Year: 2007).*
Du et al., "Improved peak detection in mass spectrum by incorporating continuous wavelet transform-based pattern matching", 2006, pp. 2059-2065 (Year: 2006).*
Daszykowski et al., "Automated alignment of one-dimensional chromatographic fingerprints", 2010, pp. 6127-6133 (Year: 2010).*
Weber et al., "Evaluation of a gas sensor array and pattern recognition for the identification of bladder cancer from urine headspace", 2010, pp. 359-364 (Year: 2010).*
Serneels et al., "Spatial Sign Preprocessing: A Simple Way to Impart Moderate Robustness to Multivariate Estimators", 2005, pp. 1402-1409 (Year: 2005).*
Aggio et al. The Use of a Gas Chromatography-Sensor System Combined With Advanced Statistical Methods, Towards the Diagnosis of Urological Malignancies. J. Breath Res. 10:1-16, 2016.
Anderssen et al. Reducing Over-Optimism in Variable Selection by Cross-Model Validation. Chemometrics and Intelligent Laboratory Systems, 84:69-74, 2006.
Boccard et al. Knowledge Discovery in Metabolomics: An Overview of MS Data Handling. J. Sep. Sci. 33:290-304, 2010.
Chen et al. Identification of Serum Biomarkers of Hepatocarcinoma Through Liquid Chromatography/ Mass Spectrometry-Based Metabonomic Method. Anal Bioanal Chem, 401:1899-1904, 2011.
Daszykowskil et al. Automated Alignment of One-Dimensional Chromatographic Fingerprints. J Chromatography A, 1217:6127-6133, 2010.
Delen et al. Analysis of Cancer Data: A Data Mining Approach. J Knowledge Eng, 26(1): 100-112, 2009.
Duo et al. Improved Peak Detection in Mass Spectrum by Incorporating Continuous Wavelet Transform-Based Pattern Matching. Bioinformatics, 22(17):2059-2065, 2006.
Filzmoser et al. Repeated Double Cross Validation. J Chemometrics, 23:160-171, 2009.
Guyon et al. Gene Selection for Cancer Classification Using Support Vector Machines. Machine Learning, 46:389-422, 2002.
Khalid et al. A Pilot Study Combining a GC-Sensor Device With a Statistical Model for the Identification of Bladder Cancer From Urine Headspace. PLOS One, 8(7): 1-8, 2013.
Kursa et al. Feature Selection With The Boruta Package. J Statistical Software, 36(11): 1-13, 2010.
Liao et al. A New Paradigm For Clinical Biomarker Discovery And Screening With Mass Spectrometry Through Biomedical Image Analysis Principles. IEEE, 2014.
Liao et al. Group-Wise Image Registration-nOrmalization (GIRO) for LC-MS Retention Time and Abundance Alignment The University of Manchester, Abstract.
Lieber and Jansen. Automated Method for Subtraction of Fluorescence From Biological Raman Spectra. Applied Spectroscopy, 57(11): 1363-1367, 2003.
Morris. Statistical Methods for Proteomic Biomarker Discovery Based on Feature Extraction or Functional Modeling Approaches. Stat Interface, 5(1): 117-135, 2012.
Mousa et al. Breast Cancer Diagnosis System Based on Wavelet Analysis and Fuzzy-Neural. Expert Systems With Applications, 28: 713-723, 2005.
Ruckstuhl et al. Baseline Subtraction Using Robust Local Regression Estimation. J. Quantitative Spectroscopy& Radiative Transfer, 68: 179-193, 2001.
Serneels et al. Spatial Sign Preprocessing: A Simple Way to Impart Moderate Robustness to Multivariate Estimators. J Chem Inf Model, 46:1402-1409, 2006.
Subasi et al. Wavelet Neural Network Classification of EEG Signals by Using AR Model With MLE Preprocessing. Neural Networks, 18: 985-997, 2005.
Van Berkel et al. Development of Accurate Classification Method Based on The Analysis of Volatile Organic Compounds From Human Exhaled Air. J Chromatography B, 861: 101-107,2008.
Weber et al. Evaluation of a Gas Sensor Array and Pattern Recognition for the Identification of Bladder Cancer From Urine Headspace. Analyst, 136: 359-364, 2011.
Zhang et al. Multiscale Peak Alignment For Chromatographic Datasets. J Chromatography A, 1223: 93-106, 2012.
GB Search Report, Application Serial No. GB1502447.4.
International Search Report, PCT/GB2016/050344.
International Preliminary Report on Patentability, PCT/GB2016/050344.
Sun Fengyu et al., "Discriminant Analysis based on Wavelet Transform in Metabolomics Liquid Chromatography Data", Chinese Health Statistics, vol. 30, No. 2, Apr. 2013, 3 pages.

* cited by examiner

METHOD AND APPARATUS FOR CREATING A CLASSIFIER INDICATIVE OF A PRESENCE OF A MEDICAL CONDITION

CROSS-REFERENCE TO RELATED APPLICATIONS

This application claims priority to International Application Serial No. PCT/GB2016/050344, filed on Feb. 12, 2016, which claims the benefit of priority to Application Serial No. GB1502447.4, filed on Feb. 13, 2015, the entireties of which are incorporated by reference.

Some embodiments of the present invention relate to a method and apparatus for determining a presence of a medical condition in a subject. In particular, although not exclusively, some embodiments of the present invention relate to a method and apparatus for determining a presence of cancer, including prostate cancer, in a subject. Some embodiments of the present invention relate to a method and apparatus for creating a classifier indicative of a presence of a medical condition in a subject.

BACKGROUND

Prostate cancer is the second most common disease worldwide for males with around 1,111,000 new cases each year. Many men with bladder outflow symptoms are often investigated for prostate cancer when they are found to have raised levels of serum PSA. However, PSA levels lacks specificity and, consequently, these men have to undergo invasive tests to confirm or refute the diagnosis of prostate cancer. In many, cancer is not found. This often leaves men worried, rather than reassured, and an endless cycle of repeated PSA level measurements may follow. Currently, PSA is not considered a diagnostic marker and has not been approved for use in screening programs in most countries. Bladder cancer is the $9^{th}$ most common cancer worldwide and the most expensive to manage. There are no biomarkers approved for follow-up and repeated cystoscopies are performed which are invasive, expensive and not without risk. Inflammatory bowel disease (IBD) is a chronic gastrointestinal disease caused by an aberrant immune response in the gut, while irritable bowel syndrome (IBS) is a disorder of the digestive tract with no known cause. There is a pressing clinical need for a better biomarker that may be used for diagnosis and screening of medical conditions including prostate cancer, prostate cancer, IBD and IBS. It would save healthcare providers money, patient misery, and also speed-up much-needed treatment for the patient.

It is an object of embodiments of the invention to at least mitigate one or more of the problems of the prior art.

STATEMENT OF INVENTION

According to aspects of the present invention, there is provided methods and apparatus as set forth in the appended claims.

According to an aspect of the present invention, there is provided a method of determining a presence of a medical condition in a subject, comprising: receiving chromatogram data indicative of a profile of volatile organic compounds in a sample from the subject; aligning the chromatogram data with reference chromatogram data; extracting one or more predetermined features from the chromatogram data using a Mexican hat wavelet transform of one or more predetermined scales; and determining whether the extracted features are indicative of the presence of a medical condition in the subject using a classifier.

BRIEF DESCRIPTION OF THE DRAWINGS

Embodiments of the invention will now be described by way of example only, with reference to the accompanying figures, in which.

DETAILED DESCRIPTION OF EMBODIMENTS OF THE INVENTION

Figure 1:
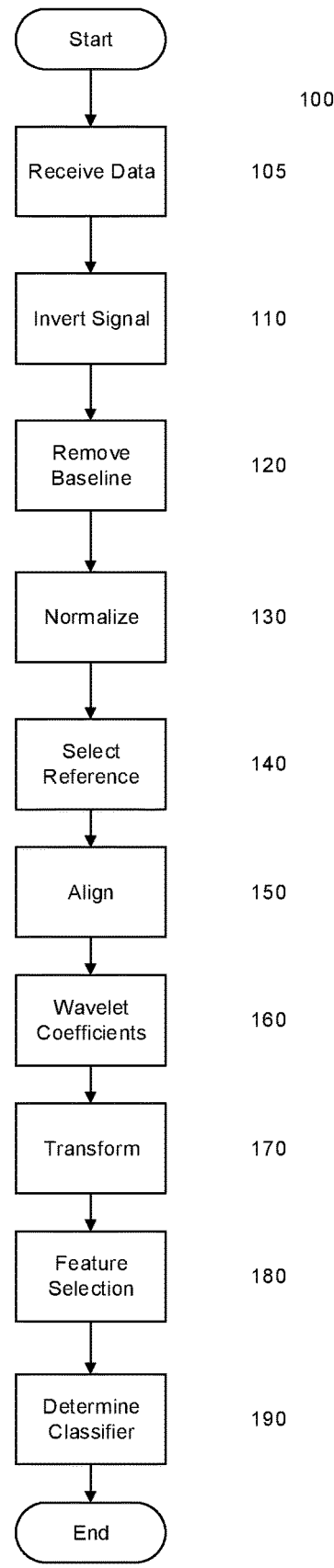
FIG. 1 shows a method according to an embodiment of the invention.

FIG. 1 illustrates a method 100 according to an embodiment of the invention. The method 100 is a method of creating a classifier indicative of whether a subject has one or more medical conditions. The medical conditions may comprise one or more of cancer, comprising bladder and/or prostate cancer, irritable bowel disease (IBD), irritable bowel syndrome (IBS), a presence of one or more predetermined bacteria such as *Clostridium difficile* (C-dif), one or more predetermined parasites, one or more predetermined fungi. The method 100 is a computer based method for creating the classifier and storing the classifier in a computer-readable medium, such as non-transitory computer-readable medium.

Figure 2:
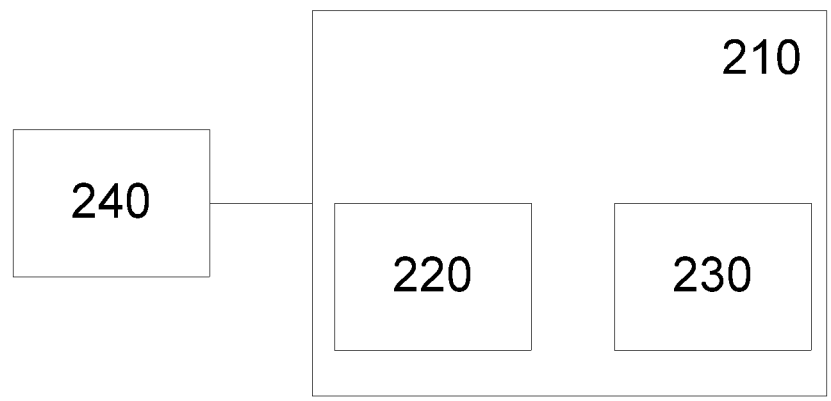
FIG. 2 shows a system according to an embodiment of the invention.

The method may be performed by an apparatus 200 according to an embodiment of the invention as illustrated in FIG. 2. The apparatus 200 comprises a control unit 210 comprising a processing unit 220 and a memory unit 230. The apparatus 210 is arranged to receive chromatogram data from a sensing unit 240. The chromatogram data is indicative of a presence of volatile compounds in a sample taken or obtained from a subject. The sample may be a sample of breath, urine or faeces from the subject, although it will be realised that this list is not exhaustive.

The sensing unit may comprise one or more Metal Oxide (MO) sensors. The sensing unit 240 may be associated with an apparatus such as described in WO/2011/061308 which is herein incorporated by reference for all purposes. The apparatus 200 may comprise a gas chromatography column coupled to the one or more sensors. The column may be associated with an oven for heating the column according to a predetermined protocol.

The chromatogram data may be communicated between the sensing unit 240 and the control unit 210 by means of a dedicated communication channel i.e. a direct electrical connection, or by means of a communication channel formed over one or more computer networks. The chromatogram data may be received at the control unit 210 in the form of one or more files each comprising chromatogram data for a respective sample.

To produce the chromatogram data, the sample may be heated according to a predetermined protocol. The protocol may define a period of heating the sample at one or more predetermined temperatures before sampling a predetermined volume of gas from the sample.

An initial temperature of the oven may be held at 40° C. for 13.4 minutes, ramped to 100° C. at a rate of 5° C./min, hold for 30 minutes and cooled to 40° C. using a temperature ramp of 10° C./minute. It will be realised that other protocols for the oven heating may be used.

A resistance of the MO sensor is determined over a period of time. The chromatogram data may comprise data indicative of a resistance of the one or more MO sensors at predetermined intervals such as 0.5 seconds, although it will be realised that other intervals may be used.

Figure 3:
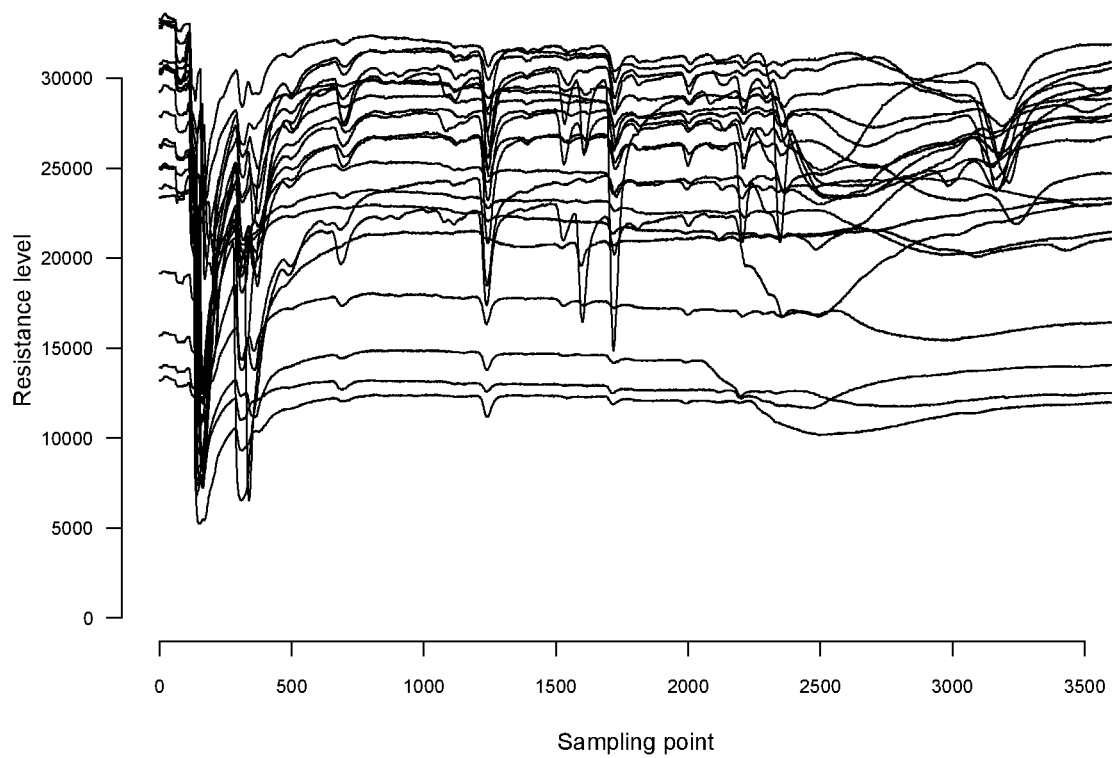
FIG. 3 shows an illustration of chromatogram data.

FIG. 3 illustrates chromatogram data according to an embodiment of the invention. FIG. 3 comprises a plot of a plurality of items of chromatogram data from respective samples. The chromatogram data is plotted over time (x-axis) and indicates a resistance (y-axis) of the sensor at each respective sample time. The chromatogram data is received by the control unit 210 in step 105. The chromatogram data may be stored in the memory unit 230 of the control unit 210.

In order to create the classifier indicative of whether a subject has one or more medical conditions, chromatogram data from a plurality of samples are provided from subjects having the respective one or more medical conditions. The classifier is based upon the chromatogram data from those subjects, as will be explained. Thus a set of chromatogram data from the plurality of samples having the one or more medical conditions is received in step 105. A further set of chromatogram data is provided from a plurality of samples not having the one or more medical conditions which may be referred to as a control set of chromatogram data.

Figure 4:
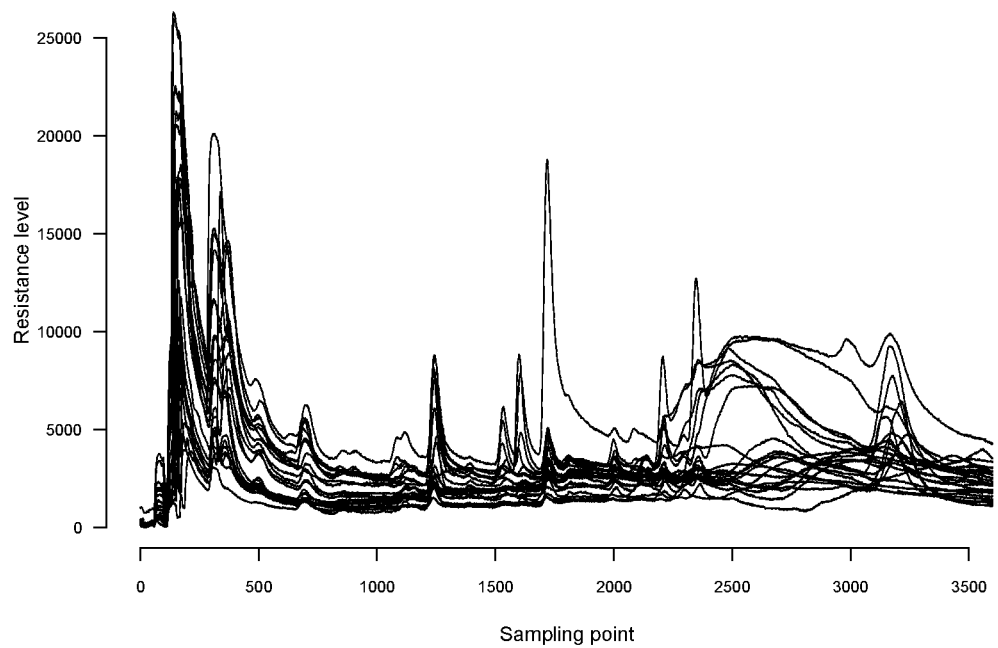
FIG. 4 shows an illustration of inverted chromatogram data according to an embodiment of the invention.

In step 110, the resistance signals of the chromatogram data received in step 105 are inverted in order to facilitate their processing using metabolomics tools. This inversion is performed individually for each sample using the following mathematical equation:

$$x=|x-(\max(x)+1)|$$

where x contains the resistance values registered for a single sample. FIG. 4 comprises a plot of the inverted chromatogram data.

In step 120 the received chromatogram data is processed. Step 120 comprises a baseline removal process. The baseline is a baseline resistance level of the chromatogram data. The baseline may be contributed as a majority, or only by, a mobile phase. The mobile phase is the gas which carries metabolites through a column of a gas chromatogram. In some embodiments the gas may be synthetic air.

A threshold may also be determined in step 120. In some embodiments the baseline of the chromatogram data is removed by a least squares-fitting process.

Figure 5:
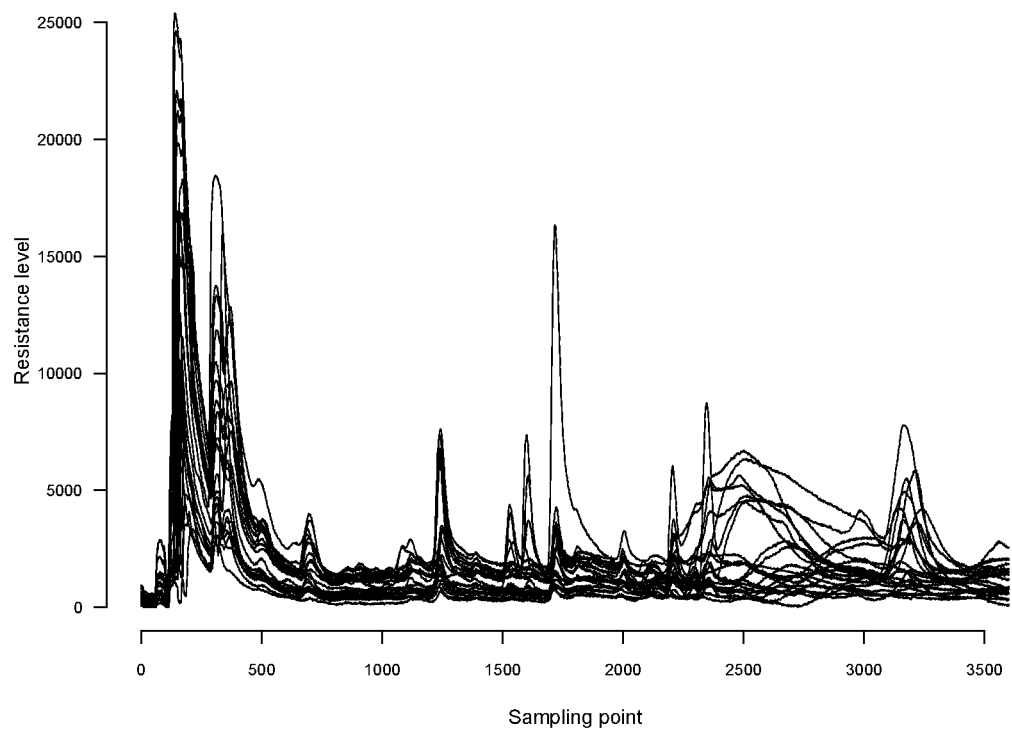
FIG. 5 shows pre-processed chromatogram data according to an embodiment of the invention.

In some embodiments step 120 further comprises determining a resistance threshold. The resistance threshold is defined as an average resistance value in the chromatogram data from a sample minus the standard deviation of its resistance values. Any resistance values lower than the resistance threshold are then set to a predetermined value, which may be zero. FIG. 5 illustrates chromatogram data processed according to an embodiment of step 120.

Figure 6:
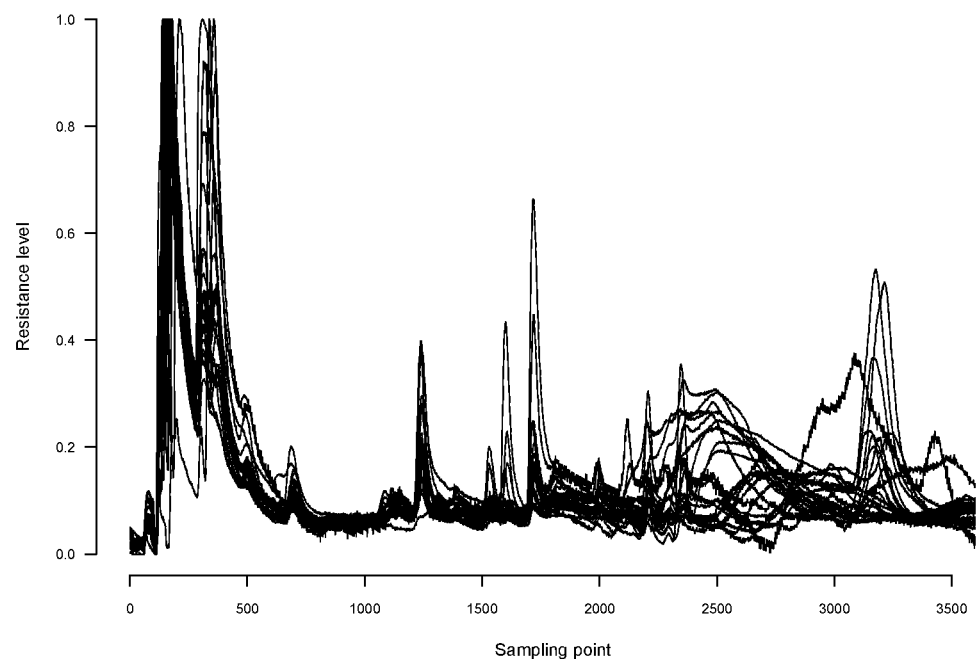
FIG. 6 shows normalized chromatogram data according to an embodiment of the invention.

In step 130 values in the chromatogram data for each sample are normalized. In one embodiment, the resistance values of a sample are normalized by dividing their values by the highest resistance value registered for the particular sample. FIG. 6 illustrates chromatogram data processed according to an embodiment of step 130.

In step 140 a reference chromatogram sample is selected for data alignment. Step 140 comprises selecting reference chromatogram data from the chromatogram data provided from step 130. In some embodiments selecting the reference chromatogram data comprises determining a coefficient indicative of correlation between each pair of chromatogram data. The coefficient may be a Pearson product-moment correlation coefficient, often referred to as a Pearson's coefficient, as will be appreciated by the skilled person.

Figure 8:
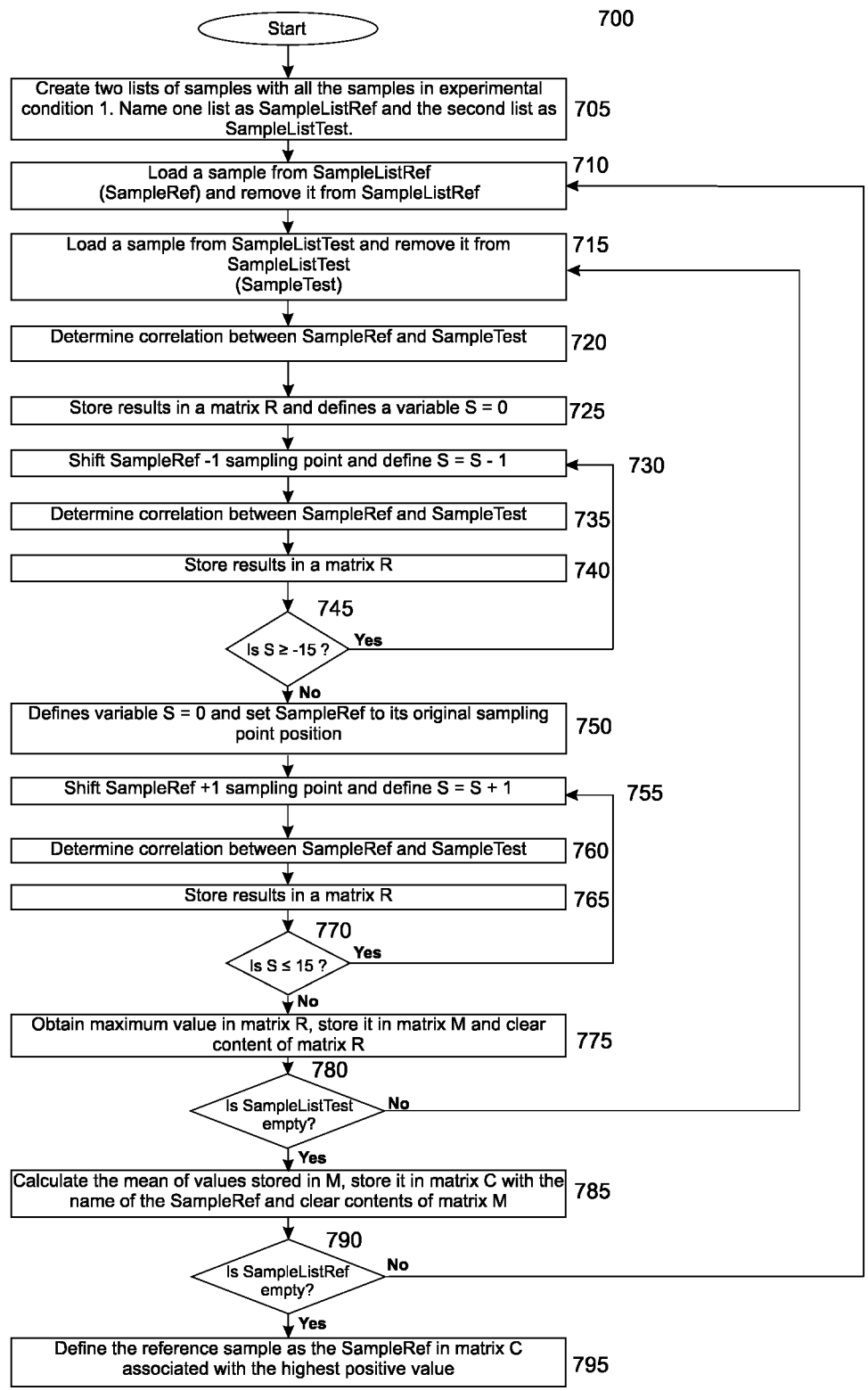
FIG. 8 shows a method of selecting the reference chromatogram sample for data alignment according to an embodiment of the invention.

A method 700 of selecting the reference chromatogram for aligning the chromatogram data according to an embodiment of the invention is illustrated in FIG. 8.

Referring to FIG. 8, in step 705 two lists containing all the samples in experimental condition 1, for example, cancer samples, are created. One of these lists may be named as SampleListRef, while the second list may be named as SampleListTest.

In step 710 a sample may be randomly selected from SampleListRef, loaded into memory and removed from SampleListRef. For clarity, this sample will be described here as SampleRef.

In step 715 a sample may be randomly selected from SampleListTest, loaded into memory and removed from SampleListTest. For clarity, this sample will be described here as SampleTest. In a first iteration of steps 710 and 715 selected samples may be first chromatograms in the data set. For example where the chromatogram data are all allocated an ID, a chromatogram having a lowest value of ID may be selected in the first iteration of steps 710 and 715.

In steps 720 and 725 the Pearson's correlation coefficient between SampleRef and SampleTest is determined and stored in a matrix, which may be named R.

In steps 730 to 765 the SampleRef is shifted a predetermined number of sampling points with a correlation coefficient with SampleTest being calculated after each sampling point shift and the resultant correlation coefficient stored in the matrix R. It will be appreciated that the SampleRef, in some embodiments, will be shifted in both positive and negative time point directions with respect to the SampleTest. In one embodiment the shift window is ±15 sampling points, although it will be realised that other sizes of shift window may be chosen.

When the SampleRef has been shifted up to the extremity or extremities of the shift window, the method moves to step 775. It will be appreciated that when arriving at step 775, in some embodiments, each chromatogram is associated with P coefficients as:

$$P=(2s+1)\times(n-1)$$

where s is a magnitude of the shift window, such as 15 (hence 2s calculating the range of shifts from negative to positive), and n is the number of samples in experimental condition 1. Therefore, in one embodiment, each chromatogram data is associated with 31 correlation coefficients for each of the remaining chromatogram data in experimental condition 1.

In step 775 the maximum value in the matrix R is obtained, stored in a new matrix named M and the contents of R are cleared or reset. Steps 715 to 775 are repeated until the SampleListTest is empty and the method moves to step 785.

In step 785 the mean value of all the values stored in M is calculated, stored in a matrix named C along with information identifying the reference sample, such as the ID of SampleRef and the contents of M are cleared. The steps 710 to 785 are repeated until SampleListRef is empty and the method moves to step 795. In step 795 the sample associated with the highest positive value in matrix C is determined as reference sample for chromatogram alignment. Step 795 may comprise storing the ID associated with the chromatogram selected as the reference chromatogram sample to allow other chromatogram data to be aligned at a later time, as will be explained.

Returning to FIG. 1, in step 150 chromatogram data is aligned. The alignment aims to ensure that the same features are compared across samples from the different data classes or medical conditions under analysis. Step 150 comprises aligning the chromatogram data in relation to the reference chromatogram sample selected at step 140. A method 800 of aligning the chromatogram data according to an embodiment of the invention is illustrated in FIG. 9.

Figure 9:
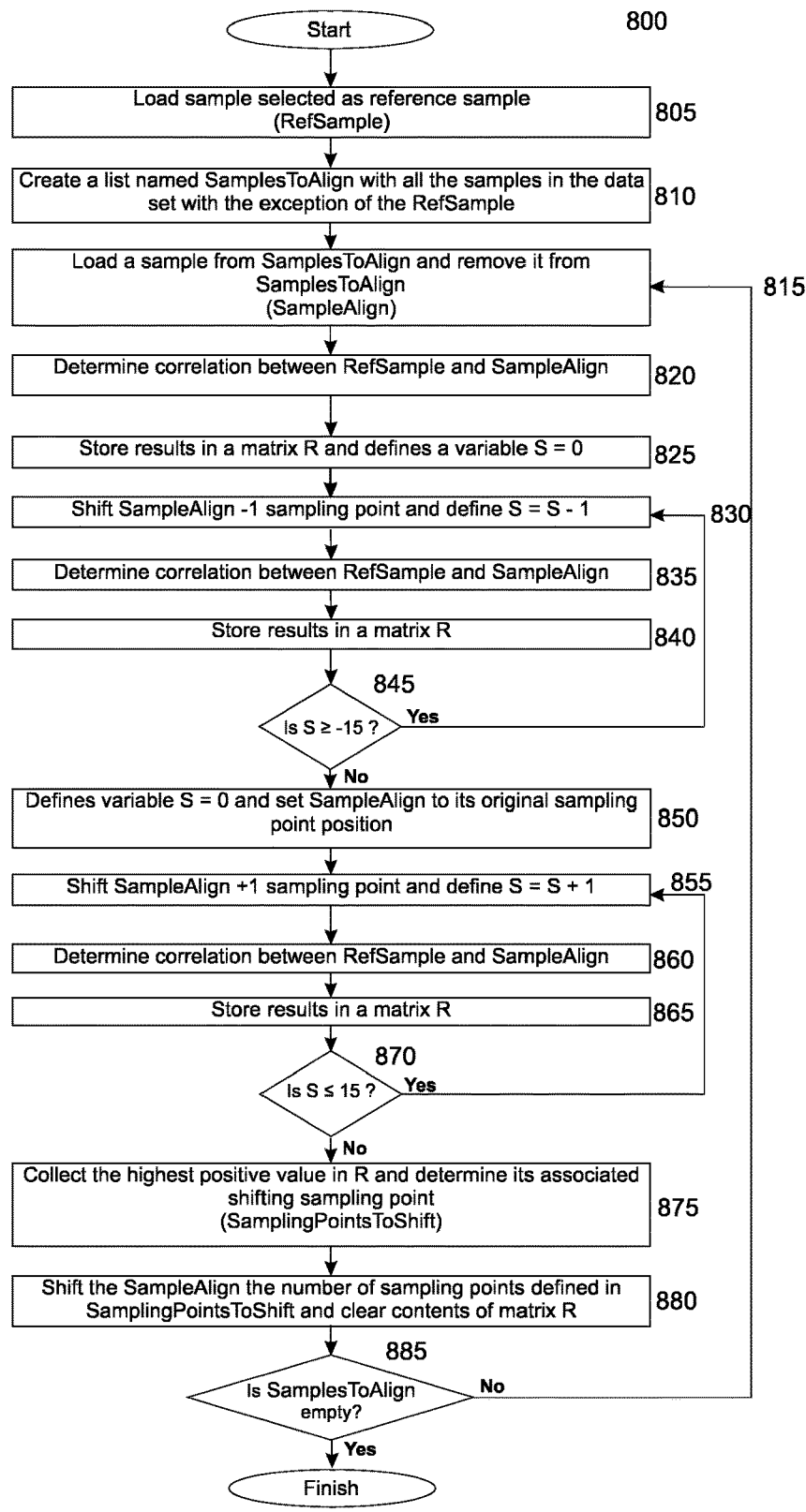
FIG. 9 shows a method of aligning chromatogram data according to an embodiment of the invention.

Referring to FIG. 9, in the method 800 every chromatogram data is aligned in relation to the reference chromatogram selected at step 140 of the FIG. 1 method 100.

In step 805 the reference chromatogram sample selected at step 140 is loaded into memory. For clarity, the reference chromatogram sample will be described here as RefSample. In step 810 a list containing all the samples in the one or more data sets under analysis, for example, Cancer and Control samples, is created. For clarity, this list will be described here as SamplesToAlign.

Figure 7:
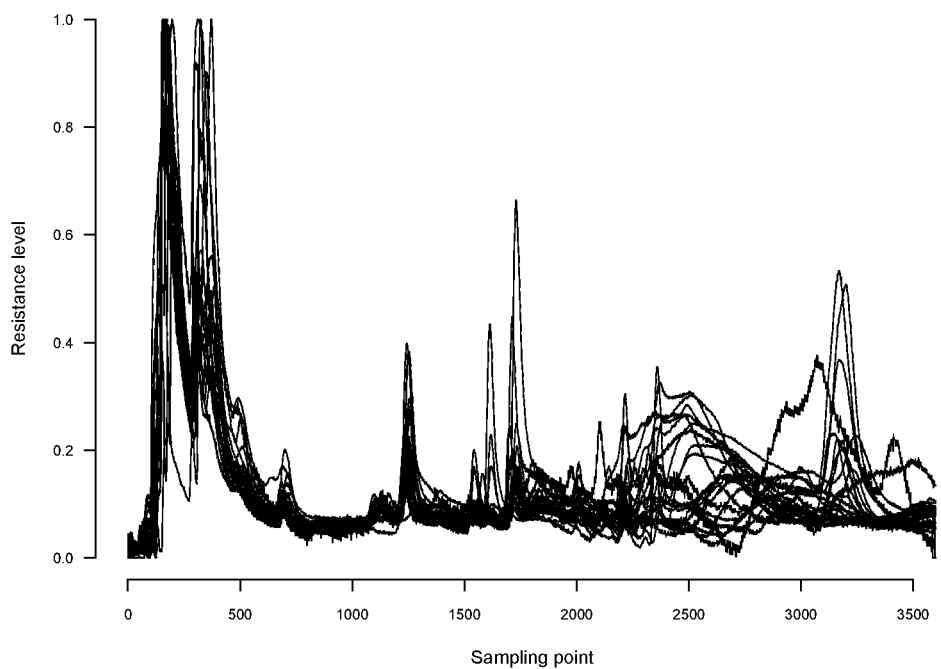
FIG. 7 shows aligned chromatogram data according to an embodiment of the invention.

In step 815 a random sample from SamplesToAlign is loaded. For clarity, this sample will be described here as SampleAlign. In steps 820 to 870 the SampleAlign is shifted a predetermined number of sampling points with a single correlation coefficient being calculated between RefSample and SampleAlign after each sampling point shift and the resultant correlation coefficient stored in the matrix R. In one embodiment the shift window is ±15 sampling points, although it will be realised that other number of time points may be chosen. It will be appreciated that the SampleAlign, in some embodiments, will be shifted in both positive and negative time point directions with respect to the RefSample. When the SampleAlign has been shifted up to the extremity or extremities of the shift window, the method moves to step 875. It will be appreciated that when arriving at step 875 in some embodiments the SampleAlign is associated with P coefficients as:

$$P=2s+1$$

where s is a magnitude of the time shift window, such as 15 (hence 2s calculating the range of time shifts from negative to positive). Therefore, in one embodiment, SampleAlign is associated with 31 correlation coefficients. In step 875 the shifting sampling point associated with the highest value in R is determined and stored as SamplingPointsToShift. In step 880 the SampleAlign is shifted the number of sampling points defined in SamplingPointsToShift and the contents of matrix R are cleared. Steps 815 to 880 are repeated until the SamplesToAlign list is empty. FIG. 7 illustrates chromatogram data aligned according to an embodiment of step 150.

Figure 10:
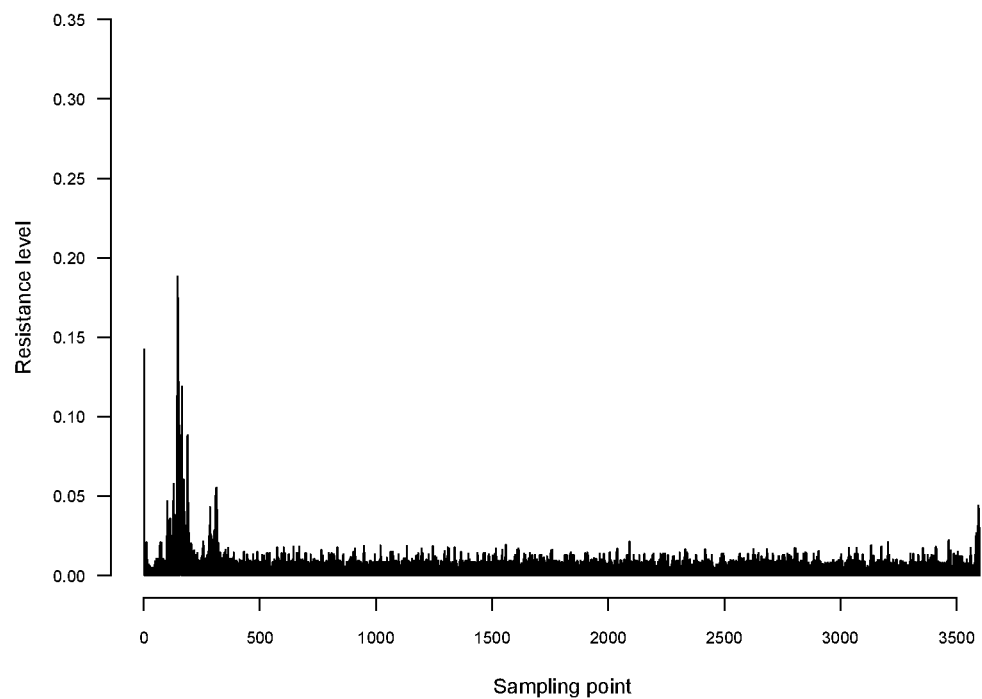
FIG. 10 shows wavelet coefficients determined for chromatogram data according to an embodiment of the invention.

Returning to FIG. 1, in step 160 the values of the aligned chromatogram data are transformed to wavelet coefficients using a Mexican hat mother wavelet, which may also be known as a Ricker Wavelet. Other mother wavelets may be used. In one embodiment the wavelet coefficients may be determined using a plurality of scales of the Mexican hat mother wavelet. The plurality of scales may be scales between lower and upper limits. In one embodiment the upper and lower limits may be 100 and 1, respectively. In one embodiment a coefficient may be determined at each integer scale between the lower and upper limits. The coefficients may be determined as a modulus of a calculated coefficient. That is, values of the chromatogram data for each sample are converted to the modulus of their wavelet coefficients using the scale of the Mexican hat mother wavelet, although the original values extracted by a Mexican hat mother wavelet may be used. The wavelet coefficients are then stored for future use, as will be explained. One of the wavelet scale values is chosen as a best match for the chromatogram data. The best match may be the wavelet scale having the highest classification accuracy, as will be explained. The accuracy of each wavelet scale may be determined based upon one or more of minimum, median, mean and maximum accuracy of a validation process. FIG. 10 illustrates chromatogram data transformed to wavelet coefficients according to an embodiment of step 160.

In step 170 one or more of log, range and SpatialSign transformation processes are applied to the chromatogram data. In one embodiment, prior to the log, range and SpatialSign transformation processes, each value of the chromatogram data has a predetermined value, such as the value 1 added to it. The chromatogram data may then be subject to log-transformation using a natural logarithm as base, although it will be realised that other base values may be used for the log-transformation. In one embodiment the range transformation is then applied to set the values of the chromatogram data to be in a predetermined range such as a range between 0 and 1. The range transformation may determine a transformed value $x_t$ at each time point of the chromatogram data where x is a data value of the chromatogram data and min(x) and max(x) are minimum and maximum value of the chromatogram data, respectively. The range transformation may be performed using the equation:

$$x_t = \frac{(x-\min(x))}{(\max(x)-\min(x))}$$

Figure 11:
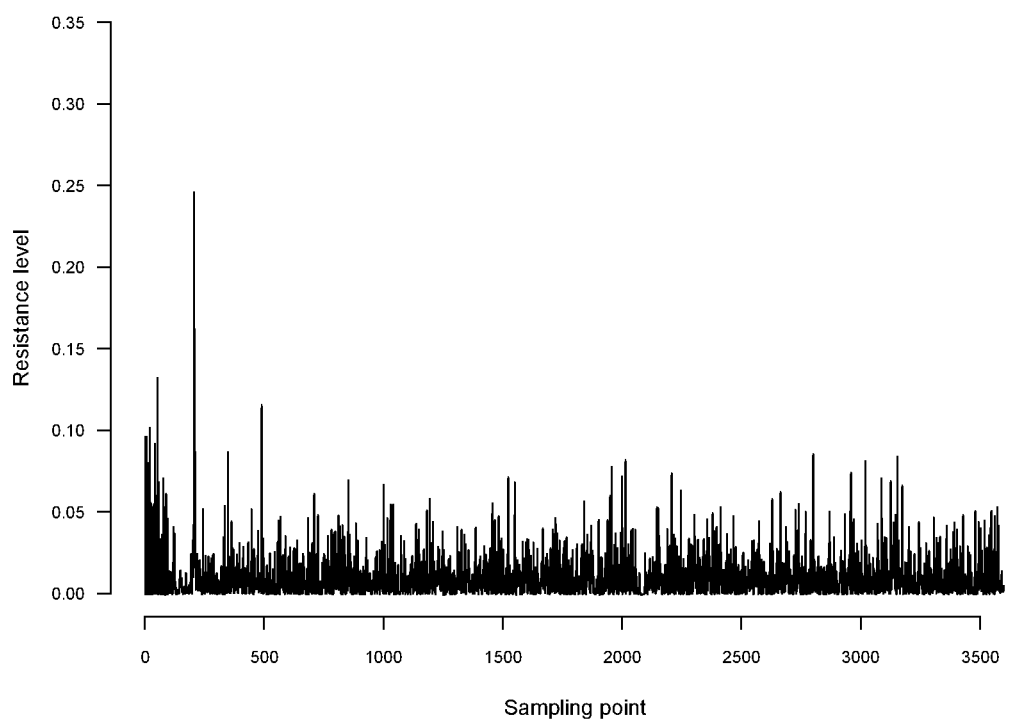
FIG. 11 shows transformed chromatogram data according to an embodiment of the invention.

In some embodiments a further transform may be applied which may be known as a Spatial Sign transform as described in *S. Serneels, E. De Nolf, P. J. Van Espen, Spatial sign preprocessing: A simple way to impart moderate robustness to multivariate estimators. Journal of Chemical Information and Modeling* 46, 1402-1409 (2006), which is herein incorporated by reference. FIG. 11 illustrates chromatogram data transformed according to an embodiment of step 170.

In step 180 one or more features of the chromatogram data are selected. The one or more features are selected to be indicative of the presence of the one or more medical conditions. In embodiments of the invention, the one or more features are selected by a feature selection algorithm using random forest. In this algorithm, decision trees are developed based on different sets of samples and random forest is used to calculate a loss of accuracy of classification when the values of features are randomly permutated between sets of samples. One or more features associated with a loss of accuracy of classification are then selected.

In some embodiments of the invention, one of two different algorithms known as boruta and rfe based on random forest are applied in step 180 in order to select the features to be used. The boruta algorithm involves the development of decision trees based on different sets of samples. Random forest is then applied to calculate the loss of accuracy of classification when the values of features are randomly permutated between sets of samples. Features associated with the loss of accuracy are then selected as indicative features. The rfe algorithm works similarly to boruta, however, it eliminates features that produce no change in the accuracy level, instead of selecting features that produce loss of accuracy. The boruta and rfe algorithms are described in Feature Selection with the Boruta Package" Journal of Statistical Software 36(11): 1-13; and Anderssen, E., K. Dyrstad, F. Westad and H. Martens (2006), "Reducing over-optimism in variable selection by cross-model validation" Chemometrics and Intelligent Laboratory Systems 84(1-2): 69-74. These references are incorporated herein by reference. In step 180 the one or more selected features are stored for later use.

In step 190 a classifier is determined. The classifier is for classifying a sample as either being a sample from a subject having the one or more medical conditions or a sample not having the one or more medical conditions. The classifier may be determined according to one of: linear discriminant analysis (LDA); partial least squares (PLS); random forest; k-nearest neighborhood (KNN); support vector machine (SVM) with radial basis function kernel (SVMRadial); SVM with linear basis function kernel (SVMLinear); and SVM with polynomial basis function kernel (SVMPoly). The classifier may be determined using, for example, a software package such as R package caret (Kuhn, M., *caret: Classification and Regression Training*. 2014).

Building and testing the classifier on the same dataset may produce biased and overoptimistic results due to potential overfitting. In step 190 a validation process may therefore be used to prevent such overfitting. The validation process may be one of repeated k-fold cross-validation and repeated double cross-validation. In particular, in exemplary embodiments of the invention two validation processes are used: 30 repeats of 10-fold cross-validation and 30 repeats of the 3-fold double cross-validation with an inner loop of 10-fold repeated 5 times. In addition, these two cross-validation processes are repeated on the same data sets, however, applying a Monte Carlo random permutation of class labels in each repeat.

As mentioned in the above description of step 160, the method 100 is repeated for a plurality of wavelet scales. The scale that produces the highest classification accuracy is then selected as the best match for the processed chromatogram data. As a result of embodiments of the method 100 illustrated in FIG. 1, a classifier is produced which is capable of classifying chromatogram data as originating from a sample having the one or more medical conditions or not having the one or more medical conditions.

Figure 12:
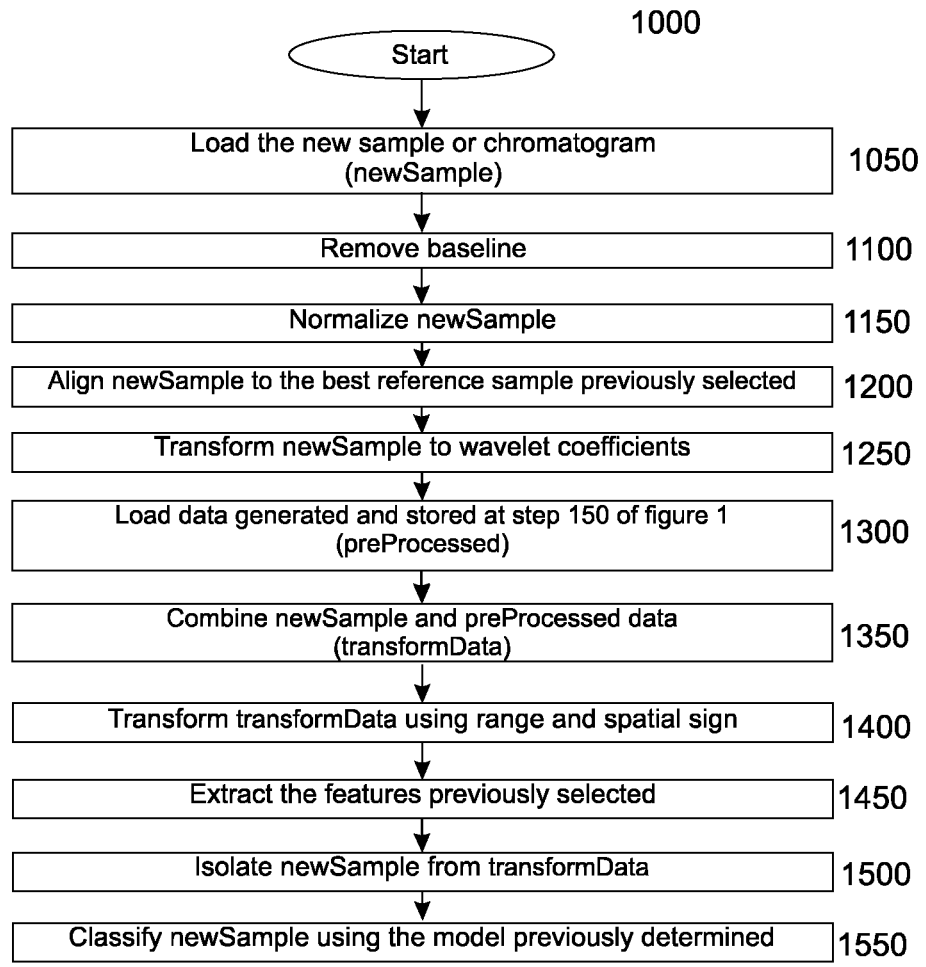
FIG. 12 illustrates a method determining a presence of a medical condition in a subject according to an embodiment of the invention.

FIG. 12 illustrates a method 1000 of determining a presence of a medical condition in a subject according to an embodiment of the invention. The method is performed upon a sample taken from the subject. The chromatogram data may be provided from an apparatus as described above with reference to FIG. 2. The same may be material excreted from the subject. The sample may be a sample of breath, urine or faeces from the subject, although it will be realised that this list is not exhaustive. As noted above, the medical condition may comprise one or more of cancer, comprising bladder and/or prostate cancer, irritable bowel disease (IBD), irritable bowel syndrome (IBS), a presence of one or more predetermined bacteria such as *Clostridium difficile* (C-dif), one or more predetermined parasites, one or more predetermined fungi.

A number of steps of the method 1000 are as-described in conjunction with the method 100 illustrated in FIG. 1. Therefore repeat description of these steps will be omitted and the reader referred to the description associated with the equivalent step in FIG. 1.

In step 1050 the chromatogram data is received. For clarity, the received chromatogram data will be described here as newSample. In some embodiments of the invention, as previously described, in step 1100 the newSample has its baseline removed and its data values are normalized in step 1150. In step 1200 the newSample is then aligned. A method 2000 of aligning the newSample according to an embodiment of the invention is illustrated in FIG. 13.

Figure 13:
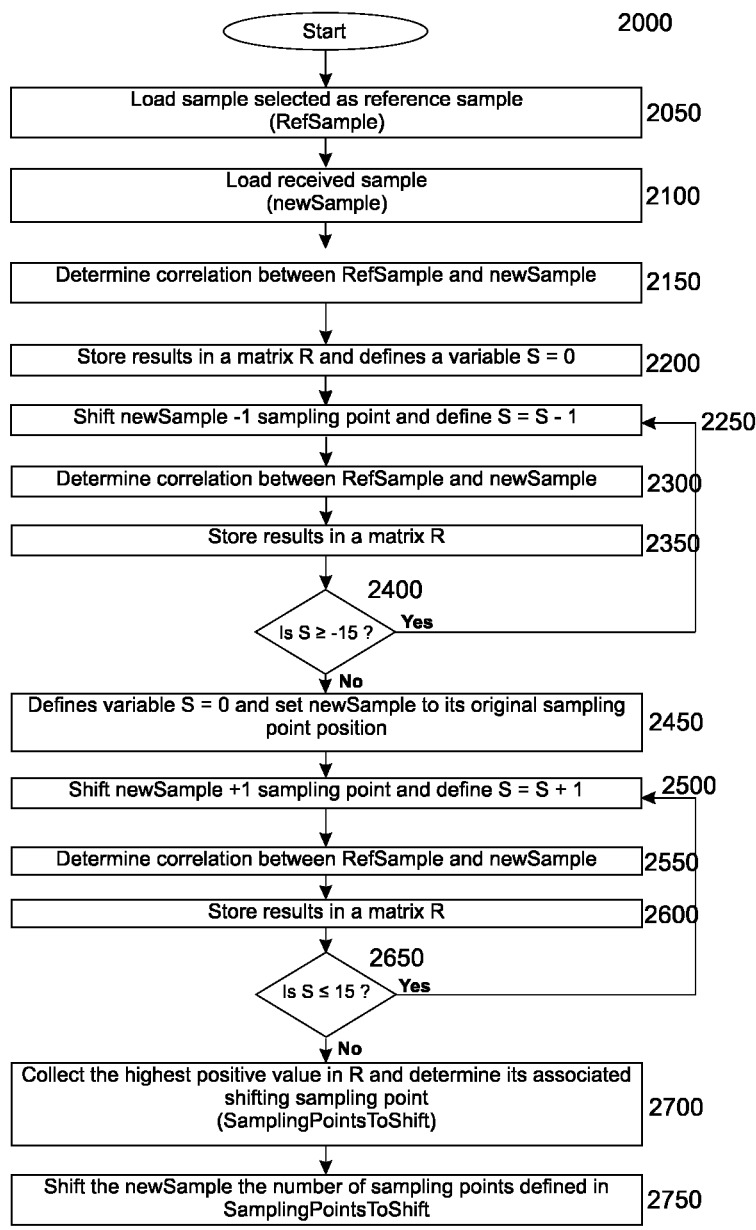
FIG. 13 shows a method of aligning received chromatogram data according to an embodiment of the invention.

Referring to FIG. 13, in step 2050 the reference chromatogram sample selected at step 140 of method 100 is loaded into memory. For clarity, the reference chromatogram data will be described here as RefSample. In step 2100 the newSample chromatogram data is loaded into memory.

In steps 2150 to 2650 the retention time of the newSample is shifted a predetermined number of sampling points with a single correlation coefficient being calculated between RefSample and newSample after each sampling point shift and the resultant correlation coefficient stored in the matrix R. In one embodiment the shift window is ±15 sampling points, although it will be realised that other number of shift points may be chosen. It will be appreciated that the newSample chromatogram data, in some embodiments, will be shifted in both positive and negative time point directions with respect to the RefSample. When the newSample chromatogram data has been shifted up to the extremity or extremities of the shift window, the method moves to step 2700. It will be appreciated that when arriving at step 2700 in some embodiments the newSample chromatogram data is associated with P coefficients as:

$$P=2s+1$$

where s is a magnitude of the time shift window, such as 15 (hence 2s calculating the range of time shifts from negative to positive). Therefore, in one embodiment, the newSample chromatogram data is associated with 31 correlation coefficients. In step 2700 the sampling point associated with the coefficient in R is determined and stored as SamplingPointsToShift. In step 2750 the newSample chromatogram data is shifted the number of sampling points defined in SamplingPointsToShift to align the new sample chromatogram data with the reference chromatogram data from the method illustrated in FIG. 1.

Returning to FIG. 12, in step 1250 the newSample chromatogram data is transformed to wavelet coefficients using a Mexican hat wavelet and a predetermined scale. The predetermined scale may be that scale determined to have produced a highest accuracy in method 100 described with reference to FIG. 1, as explained above.

In step 1300 the wavelet coefficients produced by a predetermined wavelet scale, which may be the wavelet scale associated with a highest accuracy and stored in step 160 of method 100 are loaded. The value of the wavelet scale used in step 160 of method 100 is the same as the value of the wavelet scale used in step 1250 of method 1000. For clarity, the wavelet coefficients produced in step 160 of method 100 will be described here as preProcessed data. In step 1350 the newSample is combined with the preProcessed data in a single dataset named transformData.

In step 1400 the transformData is then transformed as described in step 170 of method 100. The features defined in step 180 of method 100 are then selected from transformData. The newSample is isolated from the transformData and predicted or classified by the model determined in step 190 of method 100.

The methods described above were applied to two different datasets. First, they were applied to classify urine samples from patients with prostate cancer, bladder cancer and patients with a mixture of urological symptoms—hematuria and or prostatic symptoms (Control). Table 1 shows the results of the 30 times repeated double cross validation for the seven classifiers built. SVMRadial was able to classify prostate cancer and bladder cancer samples with 89.6% and 96.2% accuracy, respectively. Prostate and bladder cancer samples were differentiated with 93.5% accuracy. Then, the methods described above were applied to classify feces samples from patients with inflammatory bowel disease (IBD), irritable bowel syndrome (IBS) and healthy donors (Control). Tables 2 and 3 show the results of the 30 times repeated double cross validation for the seven classifiers built. IBD and IBS were differentiated from Control samples with 88.9% and 94.4%, respectively. IBD samples were differentiated from IBS samples with 85.2% accuracy. IBD samples were differentiated from non-IBD samples with 84.9% accuracy. IBS samples were differentiated from non-IBS samples with 92.1% accuracy. Finally, Control samples were differentiated from non-Control samples with 86.8% accuracy. Thus it can be appreciated that embodiments of the invention are able to determine whether a sample is from a person having a predetermined condition with accuracy.

Methods forming embodiments of the invention may be computer-implemented.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

TABLE 1

| Classifier | Accuracy (%) | | | Sensitivity (%) | | | Specificity (%) | | |
|---|---|---|---|---|---|---|---|---|---|
| | Mean | SE | Median | Mean | SE | Median | Mean | SE | Median |
| Prostate vs Control | | | | | | | | | |
| SVMRadial | 89.6 | 0.5 | 90.7 | 85.6 | 0.8 | 85.0 | 92.7 | 0.5 | 92.0 |
| SVMPoly | 88.8 | 0.4 | 88.6 | 85.5 | 0.8 | 85.0 | 91.4 | 0.6 | 91.7 |
| RF | 88.3 | 0.4 | 88.6 | 82.0 | 0.8 | 84.2 | 93.3 | 0.6 | 93.9 |
| PLS | 87.7 | 0.5 | 88.6 | 85.6 | 0.8 | 85.0 | 89.4 | 0.7 | 91.7 |
| LDA | 87.7 | 0.5 | 88.6 | 85.4 | 0.8 | 85.0 | 89.6 | 0.7 | 91.7 |
| SVMLinear | 83.8 | 0.5 | 83.7 | 81.6 | 1.0 | 82.1 | 85.5 | 0.7 | 87.5 |
| KNN | 83.0 | 0.5 | 83.0 | 81.7 | 0.8 | 84.2 | 84.0 | 0.7 | 83.7 |
| Bladder vs Control | | | | | | | | | |
| SVMPoly | 96.2 | 0.3 | 96.9 | 87.2 | 1.2 | 87.5 | 99.2 | 0.2 | 100.0 |
| SVMRadial | 96.2 | 0.3 | 96.9 | 85.0 | 1.1 | 87.5 | 99.9 | 0.1 | 100.0 |
| PLS | 94.4 | 0.4 | 93.9 | 86.3 | 1.1 | 87.5 | 97.1 | 0.4 | 98.0 |
| LDA | 93.6 | 0.5 | 93.8 | 87.4 | 1.1 | 87.5 | 95.7 | 0.5 | 95.8 |
| SVMLinear | 93.6 | 0.3 | 93.8 | 85.6 | 1.1 | 87.5 | 96.3 | 0.4 | 96.0 |
| KNN | 91.0 | 0.5 | 90.8 | 81.3 | 1.4 | 87.5 | 94.2 | 0.5 | 95.8 |
| RF | 86.8 | 0.4 | 87.5 | 46.8 | 1.6 | 50.0 | 100.0 | 0.0 | 100.0 |

TABLE 1-continued

| Classifier | Accuracy (%) | | | Sensitivity (%) | | | Specificity (%) | | |
|---|---|---|---|---|---|---|---|---|---|
| | Mean | SE | Median | Mean | SE | Median | Mean | SE | Median |
| Bladder vs Prostate | | | | | | | | | |
| SVMPoly | 93.5 | 0.4 | 92.9 | 83.5 | 1.1 | 87.5 | 97.6 | 0.4 | 100.0 |
| SVMRadial | 93.0 | 0.4 | 92.9 | 82.8 | 1.1 | 87.5 | 97.2 | 0.4 | 100.0 |
| SVMLinear | 91.8 | 0.5 | 92.6 | 85.6 | 1.5 | 87.5 | 94.4 | 0.5 | 94.7 |
| KNN | 91.2 | 0.4 | 92.6 | 81.9 | 1.2 | 87.5 | 95.1 | 0.5 | 95.0 |
| PLS | 90.9 | 0.6 | 92.6 | 80.0 | 1.5 | 87.5 | 95.3 | 0.5 | 95.0 |
| RF | 89.5 | 0.5 | 88.9 | 70.3 | 1.5 | 75.0 | 97.5 | 0.3 | 100.0 |
| LDA | 87.8 | 0.7 | 88.9 | 77.9 | 1.6 | 75.0 | 91.9 | 0.7 | 94.7 |

TABLE 2

| Classifier | Accuracy (%) | | | Sensitivity (%) | | | Specificity (%) | | |
|---|---|---|---|---|---|---|---|---|---|
| | Mean | SE | Median | Mean | SE | Median | Mean | SE | Median |
| IBD vs Control | | | | | | | | | |
| SVMPoly | 88.9 | 0.6 | 88.0 | 94.1 | 0.8 | 93.3 | 80.8 | 1.2 | 80.0 |
| SVMRadial | 86.6 | 0.7 | 87.5 | 92.8 | 0.9 | 93.3 | 77.0 | 1.3 | 77.8 |
| SVMLinear | 86.5 | 0.6 | 87.5 | 89.8 | 0.7 | 86.7 | 81.3 | 1.3 | 80.0 |
| PLS | 85.9 | 0.8 | 87.5 | 90.3 | 1.0 | 93.3 | 79.2 | 1.5 | 80.0 |
| LDA | 85.9 | 0.7 | 85.8 | 89.3 | 0.9 | 93.3 | 80.6 | 1.2 | 80.0 |
| RF | 84.9 | 0.6 | 84.0 | 95.6 | 0.5 | 100 | 68.2 | 1.5 | 70.0 |
| KNN | 82.4 | 0.7 | 83.3 | 91.9 | 0.8 | 93.3 | 67.6 | 1.5 | 70.0 |
| IBS vs Control | | | | | | | | | |
| SVMRadial | 94.4 | 0.6 | 94.4 | 93.9 | 1.0 | 100 | 94.9 | 0.8 | 100 |
| SVMPoly | 94.4 | 0.5 | 94.4 | 94.0 | 1.0 | 100 | 94.8 | 0.7 | 100 |
| SVMLinear | 93.4 | 0.6 | 94.4 | 93.2 | 1.2 | 100 | 93.6 | 0.7 | 90.0 |
| PLS | 92.9 | 0.7 | 94.4 | 90.1 | 1.1 | 87.5 | 95.3 | 0.8 | 100 |
| RF | 92.9 | 0.7 | 94.4 | 92.2 | 1.1 | 100 | 93.5 | 0.8 | 90.0 |
| KNN | 91.9 | 0.7 | 94.1 | 91.3 | 1.1 | 87.5 | 92.6 | 0.9 | 90.0 |
| LDA | 78.7 | 1.1 | 77.8 | 76.8 | 1.4 | 75.0 | 80.3 | 1.7 | 80.0 |
| IBD vs IBS | | | | | | | | | |
| RF | 85.2 | 0.6 | 87.0 | 96.3 | 0.5 | 100 | 64.4 | 1.8 | 62.5 |
| SVMRadial | 82.2 | 0.7 | 82.6 | 90.7 | 0.9 | 93.3 | 66.1 | 1.8 | 62.5 |
| SVMPoly | 82.2 | 0.7 | 82.6 | 91.6 | 0.8 | 93.3 | 64.6 | 2.0 | 62.5 |
| SVMLinear | 81.6 | 0.8 | 82.6 | 85.6 | 1.1 | 86.7 | 74.0 | 1.7 | 75.0 |
| PLS | 80.3 | 0.8 | 82.6 | 89.0 | 0.8 | 86.7 | 64.0 | 1.7 | 62.5 |
| KNN | 77.7 | 0.8 | 78.3 | 91.7 | 0.9 | 93.3 | 51.5 | 1.9 | 50.0 |
| LDA | 75.3 | 0.9 | 78.3 | 82.1 | 1.1 | 86.7 | 62.5 | 2.0 | 62.5 |

TABLE 3

| Classifier | Accuracy (%) | | | Sensitivity (%) | | | Specificity (%) | | |
|---|---|---|---|---|---|---|---|---|---|
| | Mean | SE | Median | Mean | SE | Median | Mean | SE | Median |
| IBD vs non-IBD | | | | | | | | | |
| SVMPoly | 84.9 | 0.5 | 84.8 | 82.2 | 1.0 | 80.0 | 87.2 | 0.8 | 88.6 |
| SVMRadial | 84.0 | 0.5 | 84.4 | 80.1 | 1.0 | 80.0 | 87.3 | 0.8 | 88.2 |
| SVMLinear | 82.8 | 0.7 | 81.8 | 81.4 | 1.2 | 80.0 | 84.1 | 1.0 | 83.3 |
| RF | 81.9 | 0.7 | 81.8 | 79.5 | 1.1 | 80.0 | 84.0 | 1.0 | 83.3 |
| LDA | 81.5 | 0.5 | 81.8 | 80.7 | 1.0 | 80.0 | 82.2 | 0.8 | 83.3 |
| PLS | 80.4 | 0.5 | 81.3 | 78.8 | 1.1 | 80.0 | 81.7 | 0.9 | 82.4 |
| KNN | 76.5 | 0.7 | 75.8 | 75.3 | 1.1 | 73.3 | 77.6 | 1.0 | 77.8 |
| IBS vs non-IBS | | | | | | | | | |
| PLS | 92.1 | 0.5 | 90.9 | 80.3 | 1.5 | 81.3 | 96.0 | 0.4 | 96.0 |
| SVMRadial | 89.7 | 0.4 | 90.6 | 61.4 | 1.7 | 62.5 | 98.9 | 0.2 | 100.0 |
| SVMLinear | 89.6 | 0.5 | 90.6 | 78.6 | 1.6 | 75.0 | 93.2 | 0.5 | 92.0 |
| SVMPoly | 89.5 | 0.4 | 90.6 | 66.1 | 1.6 | 62.5 | 97.1 | 0.4 | 100.0 |

TABLE 3-continued

| Classifier | Accuracy (%) | | | Sensitivity (%) | | | Specificity (%) | | |
|---|---|---|---|---|---|---|---|---|---|
| | Mean | SE | Median | Mean | SE | Median | Mean | SE | Median |
| LDA | 88.6 | 0.5 | 87.9 | 76.8 | 1.6 | 75.0 | 92.4 | 0.6 | 92.0 |
| RF | 83.4 | 0.5 | 84.4 | 36.9 | 1.9 | 37.5 | 98.5 | 0.2 | 100.0 |
| KNN | 82.9 | 0.5 | 81.8 | 39.2 | 1.9 | 37.5 | 97.0 | 0.4 | 96.0 |
| Control vs non-Control | | | | | | | | | |
| SVMPoly | 86.8 | 0.4 | 87.5 | 64.5 | 1.6 | 60.0 | 96.2 | 0.5 | 95.7 |
| SVMRadial | 85.0 | 0.4 | 84.8 | 61.2 | 1.7 | 60.0 | 95.1 | 0.5 | 95.7 |
| LDA | 85.0 | 0.6 | 86.2 | 74.6 | 1.6 | 77.8 | 89.5 | 0.7 | 91.3 |
| SVMLinear | 84.5 | 0.6 | 84.8 | 73.5 | 1.6 | 77.8 | 89.2 | 0.7 | 91.3 |
| RF | 83.5 | 0.5 | 84.4 | 51.0 | 1.9 | 50.0 | 97.2 | 0.3 | 95.7 |
| PLS | 82.8 | 0.7 | 84.4 | 67.3 | 1.5 | 70.0 | 89.4 | 0.8 | 91.3 |
| KNN | 80.2 | 0.6 | 81.3 | 54.0 | 1.9 | 55.6 | 91.2 | 0.6 | 91.3 |

The invention claimed is:

1. A method of creating a classifier indicative of a presence of a medical condition in a subject, comprising:
receiving chromatogram data indicative of a profile of volatile organic compounds in a sample from each of a first plurality of subjects having the medical condition and a second plurality of subjects without the medical condition, wherein the chromatogram data is indicative of a resistance of one or more metal oxide sensors associated with a gas chromatography column over a period of time;
selecting one of the chromatogram data as reference chromatogram data;
aligning the remaining chromatogram data in relation to the reference chromatogram data;
extracting one or more features from the chromatogram data using a Mexican hat wavelet transform of a plurality of scales to determine a coefficient for the chromatogram data at each of the plurality of scales of the Mexican hat wavelet;
selecting one of the plurality of scales as a best match for the chromatogram data based on an accuracy of a validation process;
selecting one or more features of the chromatogram data indicative of the medical condition; and
constructing a classifier for determining a boundary between chromatogram data indicative of the medical condition and chromatogram data indicative of an absence of the medical condition.

2. The method of claim 1, wherein the selecting the reference chromatogram data comprises:
determining a correlation coefficient between each of a first plurality of chromatogram data; and
selecting chromatogram data having a highest positive correlation coefficient as the reference chromatogram data.

3. The method of claim 2, wherein:
the correlation coefficient is determined between each of the first plurality of chromatogram data at each of a plurality of sample points within a predetermined shift window; and
the selecting the chromatogram data comprises selecting a shift interval of the chromatogram data having a highest positive correlation coefficient.

4. The method of claim 3, wherein remaining chromatogram data is aligned in relation to the sample point of the reference chromatogram data having the highest positive correlation coefficient.

5. The method of claim 2, wherein the correlation coefficient is a Pearson product-moment correlation coefficient.

6. The method of claim 1, wherein the plurality of scales are between upper and lower limits.

7. The method of claim 6, wherein the coefficient is determined at each integer scale between the upper and lower limits.

8. The method of claim 1, wherein the one or more features of the chromatogram data indicative of the medical condition are selected using a selection algorithm based upon random forest.

9. The method of claim 8, wherein in said algorithm one or more features of the chromatogram data are selected which, when omitted, lead to a loss of accuracy.

10. The method of claim 1, comprising transforming a range of the chromatogram data.

11. The method of claim 10, wherein the range transformation is applied to set the values of the chromatogram data to be in a predetermined range.

12. The method of claim 10, wherein the range of the chromatogram data is transformed according to the equation:

$$x_t = \frac{(x - \min(x))}{(\max(x) - \min(x))}$$

where a transformed value $x_t$ at each time point of the chromatogram data where x is a data value of the chromatogram data and min(x) and max(x) are minimum and maximum value of the chromatogram data.

13. The method of claim 1, wherein the classifier is constructed according to one of: linear discriminant analysis (LDA); partial least squares (PLS); random forest; k-nearest neighborhood (KNN); support vector machine (SVM) with radial basis function kernel (SVMRadial); SVM with linear basis function kernel (SVMLinear); and SVM with polynomial basis function kernel (SVMPoly).

14. A method of determining a presence of a medical condition in a subject, comprising:
receiving chromatogram data indicative of a profile of volatile organic compounds in a sample from the subject;
aligning the chromatogram data with reference chromatogram data;
extracting one or more predetermined features from the chromatogram data using a Mexican hat wavelet transform of one or more predetermined scales wherein the one or more predetermined features are features selected in a method according to claim 1; and determining whether the extracted features are indicative of the presence of a medical condition in the subject using the classifier constructed according to claim 1.

15. The method of claim 14, wherein the determining whether the extracted features are indicative of the presence of the medical condition in the subject is based upon values of the extracted features.

16. The method of claim 14, wherein the aligning the chromatogram data comprises:
   determining a correlation coefficient between the chromatogram data and the reference chromatogram data at each of a plurality of sample points within a predetermined shift window; and
   aligning the chromatogram data to the reference chromatogram data at a sample point time having a greatest correlation coefficient.

17. The method of claim 16, wherein the correlation coefficient is a Pearson's coefficient.

18. The method of claim 14, wherein the reference chromatogram data is selected in a method of creating the classifier.

19. The method of claim 14, wherein the reference chromatogram data is chromatogram data associated with a predetermined identifier.

20. The method of claim 14, wherein the extracting one or more predetermined features comprises:
   obtaining data indicative of a scale of the Mexican hat wavelet transform; and
   converting the chromatogram data to a modulus of wavelet coefficients using the scale of the Mexican hat wavelet transform.

21. The method of claim 14, comprising obtaining feature information indicative of the one or more predetermined features to be extracted.

22. The method of claim 14, comprising transforming a range of the chromatogram data.

23. The method of claim 22, wherein the range transformation is applied to set the values of the chromatogram data to be in a predetermined range.

24. The method of claim 14, comprising applying a SpatialSign transformation process to the chromatogram data.

25. The method of claim 14, comprising combining the chromatogram data with pre-processed chromatogram data.

26. A non-transitory computer-readable medium comprising instructions which, when executed by a computer, is arranged to perform a method according to claim 1.

27. An apparatus arranged to create a classifier indicative of a presence of a medical condition in a subject, wherein the apparatus is arranged to receive from a sensing unit chromatogram data indicative of a profile of volatile organic compounds in a sample from each of a first plurality of subjects having the medical condition and a second plurality of subjects without the medical condition, wherein the chromatogram data is indicative of a resistance of one or more metal oxide sensors associated with a gas chromatography column over a period of time;
   the apparatus comprising a processing unit and a memory unit storing computer executable instructions which, when executed by the processing unit, cause the processing unit to:
   select one of the chromatogram data as reference chromatogram data;
   align the remaining chromatogram data in relation to the reference chromatogram data;
   extract one or more features from the chromatogram data using a Mexican hat wavelet transform of a plurality of scales to determine a coefficient for the chromatogram data at each of the plurality of scales of the Mexican hat wavelet;
   selecting one of the plurality of scales as a best match for the chromatogram data based on an accuracy of a validation process;
   select one or more features of the chromatogram data indicative of the medical condition; and
   construct a classifier for determining a boundary between chromatogram data indicative of the medical condition and chromatogram data indicative of an absence of the medical condition.

* * * * *